United States Patent [19]

Yamada et al.

[11] Patent Number: 5,017,191
[45] Date of Patent: May 21, 1991

[54] INJECTOR

[75] Inventors: Hideo Yamada; Shozo Nakayama, both of Hyogo; Mitsuhisa Iinuma, Aichi; Hisao Tobiki, Hyogo, all of Japan

[73] Assignee: Nihon Medi-Physics Co., Ltd., Takarazuka, Japan

[21] Appl. No.: 320,608

[22] Filed: Mar. 8, 1989

[30] Foreign Application Priority Data

Mar. 11, 1988 [JP] Japan ............... 63-32868[U]

[51] Int. Cl.$^5$ ............................................. A61M 5/00
[52] U.S. Cl. .................................................. 604/243
[58] Field of Search ............................ 604/240–243, 604/122, 124, 125

[56] References Cited

U.S. PATENT DOCUMENTS

| | | | |
|---|---|---|---|
| 1,746,009 | 2/1930 | Mulford | 604/243 |
| 3,063,450 | 11/1962 | Myerson et al. | 604/240 |
| 3,096,763 | 7/1963 | McConnaughey et al. | 604/249 |
| 3,234,944 | 2/1966 | Stevens et al. | 604/240 |
| 3,974,832 | 8/1976 | Kruck | 604/242 |
| 3,989,044 | 11/1976 | Meierhoefer | 604/243 |
| 4,240,423 | 12/1980 | Akhavi | 604/272 |
| 4,340,068 | 7/1982 | Kaufman | 604/125 |
| 4,398,544 | 8/1983 | Nugent et al. | 604/240 |
| 4,435,176 | 3/1984 | Ishikawa | 604/240 |
| 4,689,047 | 8/1987 | Bauer | 604/122 |
| 4,781,701 | 11/1988 | Geprägs | 604/240 |

FOREIGN PATENT DOCUMENTS

| | | | |
|---|---|---|---|
| 0444267 | 5/1950 | Italy | 604/241 |
| 49-89395 | 8/1974 | Japan . | |
| 0298179 | 10/1928 | United Kingdom | 604/241 |
| 1444119 | 7/1976 | United Kingdom . | |

Primary Examiner—C. Fred Rosenbaum
Assistant Examiner—Sharon Rose
Attorney, Agent, or Firm—Jones, Tullar & Cooper

[57] ABSTRACT

An injector pre-filled with a radiopharmaceutical liquid, which comprises (1) a syringe containing a radiopharmaceutical liquid with a stopper made of an elastic material fitted at the top opening, (2) a holder having a hole at thee central part fitted on the stopper to keep it firmly at such position, (3) an adaptor having a body portion of which the lower part forms a cap portion, a passage for the radiopharmaceutical liquid penetrating the body portion and a hollow needle portion continuously extending from the passage to the lower direction, detachably fitted on the syringe, and (4) a disposable needle head comprising a needle having a passage for the radiopharmaceutical liquid therein and a cap portion, detachably fitted on the body portion of said adaptor to make a gap at the top part of the cap portion of the needle head, the cap portion of the needle head being at least partly made of an inside observable material.

3 Claims, 1 Drawing Sheet

INJECTOR

BACKGROUND OF THE INVENTION

The present invention relates to an injector for medical treatment. More particularly, it relates to an injector filled with a pharmaceutical liquid, i.e. so-called "prefilled syringe".

For the convenience of handling, there are widely used disposable injectors filled with a pharmaceutical these days. Particularly in the field of nuclear medicine, the use of such disposable injectors filled with a radiopharmaceutical liquid is favored to protect the operators such as physicians, nurses, etc. from radiation exposure.

A typical example of conventional injectors used for the purpose is shown in FIG. 1 of the accompanying drawings. However, such conventional injectors have certain drawbacks. For instance, a double-sided needle is used for the injectors so that whether the blood vessel is rightly secured with the needle can not be confirmed until the blood comes into the syringe (i.e. the cylinder). When a radiopharmaceutical liquid is to be administered, confirmation becomes more difficult, because the cylinder in such case is usually covered with lead or the like for prevention of radiation exposure While needles having various diameters, normally of 18 to 26 gauges, are to be used depending on age, administration site, etc., it is particularly difficult for ordinary hospitals to have a sufficient number and variety of such special needles as disposable double-sided needles

SUMMARY OF THE INVENTION

A main object of the present invention is to provide an injector by which proper securing of the blood vessel with the needle can be readily and quickly confirmed and for which a normal (i.e. one-sided) needle can be used. Advantageously, the injector can be designed to be relatively small in size so that the amount of the waste material to be disposed can be kept small.

The injector of this invention comprises (1) a syringe (i.e. cylinder) containing a pharmaceutical liquid with a stopper made of an elastic material (e.g. rubber) fitted at the top opening of the syringe, (2) a holder fitted on the stopper so as to keep said stopper firmly at the top opening, (3) an adaptor comprising a body portion of which the lower part forms a cap portion, a passage for the pharmaceutical liquid penetrating the body portion and a hollow needle portion extending from the passage to the lower direction, detachably fitted on the holder, and (4) a disposable needle head comprising a needle having a passage for the pharmaceutical liquid therein and a cap portion, detachably fitted on the body portion of the adaptor to make a gap at the top part of the cap portion, the cap portion of the disposable needle head being at least partly made of an inside observable material

BRIEF DESCRIPTION OF THE DRAWINGS

This invention will be hereinafter explained more in detail with reference to the accompanying drawings wherein.

DETAILED DESCRIPTION

Figure 1:
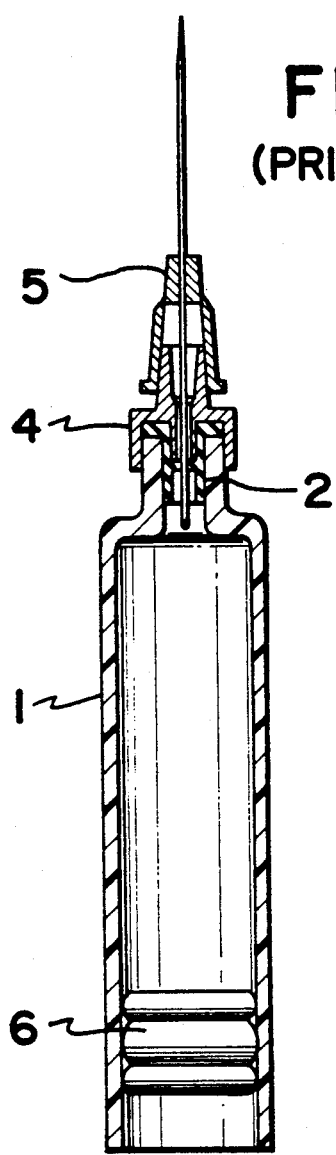
FIG. 1 is a sectional view of a conventional injector.

The numerals in the drawings have the following designations; 1, syringe; 2, stopper; 3, holder; 4, adaptor; 5, needle head; 6, gasket; 7, gap.

In FIG. 1 showing the section of a conventional disposable injector, the syringe 1 is filled with a pharmaceutical liquid and has a gasket 6 at the bottom part, the gasket being detachably provided with a plunger (not shown). At the top opening of the syringe 1, a stopper 2 is fitted, and the stopper 2 is firmly kept at that position with an adaptor 4 serving also as a holder fitted thereon. On the adaptor 4, a needle head 5 provided with a double-sided needle is detachably fitted. When the needle head 5 is fitted on the adaptor 4, the lower end of the double-sided needle penetrates the stopper 2 at the center so as to make a passage for the pharmaceutical liquid, which is to be administered into a patient by pressing the gasket 6 with the plunger.

Figure 2:
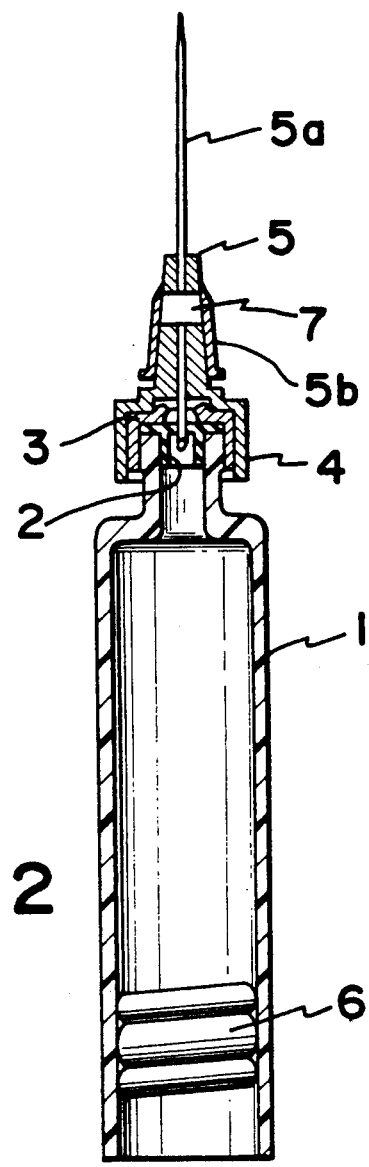
FIG. 2 is a sectional view of an injector as an embodiment of the invention, i.e. comprising a syringe, a stopper and a holder fitted at the top opening of the syringe, an adaptor detachably fitted on the holder and a disposable needle head detachably fitted on the adaptor.
Figure 3:
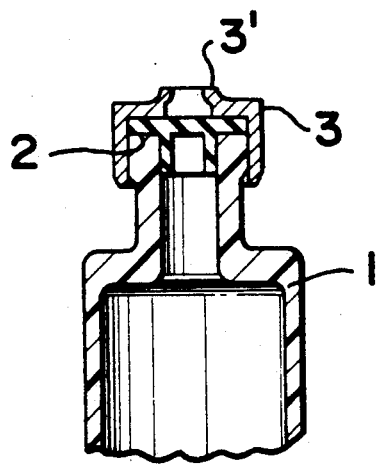
FIG. 3 is a sectional view of the top portion of a syringe fitted with a stopper and a holder according to the invention.
Figure 4:
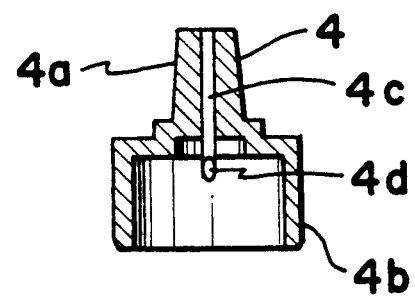
FIG. 4 is a sectional view of an adaptor to be detachably fitted on a holder according to the invention.

The injector of the invention has a similar structure to that of the conventional injector. In FIG. 2 the section of a disposable injector according to the invention is shown, FIG. 3 shows the section of the top portion of the syringe of such injector fitted with a stopper and a holder, and FIG. 4 shows the section of an adaptor to be detachably fitted on the holder, the syringe 1 is filled with a pharmaceutical liquid and has a gasket 6 at the bottom part, the gasket being detachably provided with a plunger (not shown). At the top opening of the syringe 1, a stopper 2 made of an elastic material is fitted, and the stopper 2 is firmly kept at that position with a holder 3 fitted thereon, the holder 3 having a hole at the central part and preferably provided with a projection 3' at the fringe of the hole. On the holder 3, an adaptor 4 comprising a body portion 4a of which the lower part forms a cap portion 4b, a passage 4c for the pharmaceutical liquid penetrating the body portion and a hollow needle portion 4d extending from the passage in the lower direction is detachably fitted. On the adaptor 4, a needle head 5 comprising a needle (one-sided needle) 5a and a cap portion 5b is detachably fitted in such a manner that a space 7 is formed at the top part and inside of the cap portion 5b. When the adaptor 4 as previously fitted with the needle head 5 thereon is fitted on the holder 3, the lower end of the needle portion 4d penetrates the stopper 2 at the center so as to make a passage for the pharmaceutical liquid, which is to be administered into a patient by pressing the gasket 6 with the plunger. The cap portion 5b is made of a material which makes it possible to observe the inside from the outside, e.g. a transparent or semi-transparent plastic material at least at the part corresponding to the gap 7.

In order to ensure exact fitting between the syringe 1 and the adaptor 4, the holder 3 is preferably made of a plastic material, which makes the tolerance between the two elements smaller. Provided that any appropriate contrivance is made to reduce the tolerance, the use of an aluminum material or any other material for the holder 3 is also allowable. For holding and fixing the holder 3 and the adaptor 4 on the syringe 1, any conventional means such as screwing, bayonet type fitting or coupling may be adopted.

The upward projection 3' on the fringe of the hole at the outer surface of the holder 3 is to fix a lid for maintaining the sterile state at the top of the stopper 2. Such projection is not essential and may be omitted or replaced by any other means; for instance, the sterile state may be kept by accommodating the entire body of the syringe 1 with the stopper 2 and the holder 3 in a sterile bag.

By taking the construction as above, the injection needle can be made smaller in length Also, the body portion of the adaptor 4 may be designed to fit with the cap portion of an ordinary disposable needle (one-sided needle), and therefore it is possible to use needles having various gauges depending on the use. Further, the security of the blood vessel can be readily ascertained through the gap 7.

For practical use, (a) a syringe 1 containing a pharmaceutical liquid and sealed at the top opening with a stopper 2 by the aid of a holder 3, (b) an adaptor 4 to be fitted on the top opening of the syringe 1 and (c) a disposable needle head 5 may be separately supplied to the operators such as physicians, nurses or the like. In use, the adaptor 4 is fitted with the disposable needle head 5 on the body portion and then fitted on the top opening of the syringe 1 so as to make the needle portion 4d of the adaptor 4 penetrated through the stopper 2, whereby the passage for the pharmaceutical liquid is completed from the syringe 1 to the tip of the needle head 5. Administration of the pharmaceutical liquid to a patient may be then carried out in a usual way.

What is claimed is:

1. An injector pre-filled with a radiopharmaceutical liquid, which comprises:
    a syringe containing the radiopharmaceutical liquid, said syringe having a top opening;
    a stopper made of an elastic material fitted at said top opening;
    a holder having a central part with a hole therethrough, said holder being fitted on the stopper to keep it firmly in position at said top opening;
    an adaptor having a body portion of which the lower part forms a cap portion, a passage for the radiopharmaceutical liquid penetrating the body portion, and a hollow needle portion continuously extending from the passage in the lower direction, said adaptor being detachably fitted on said syringe, the stopper being pierceable by the needle portion extending from said adaptor; and
    a disposable needle head comprising a needle having a passage for the radiopharmaceutical liquid therein and a cap portion, said disposable needle head being detachably fitted on the body portion of said adaptor to form a gap at the top part of the cap portion of said needle head, the cap portion of said needle head being, at least partly, made of an inside observable material.

2. The injector according to claim 1, wherein the holder is made of a plastic material.

3. The injector according to claim 1, wherein the holder is made of an aluminum material.

* * * * *